United States Patent [19]

Pauling et al.

[11] Patent Number: 4,463,180

[45] Date of Patent: Jul. 31, 1984

[54] PROCESS AND INTERMEDIATES FOR THE MANUFACTURE OF (3aS, 6aR)-1,3-DIBENZYLDIHYDRO-1H-FURO[3,4-d] IMIDAZOLE-2,4(3H,3aH)-DIONE

[75] Inventors: Horst Pauling, Bottmingen; Christof Wehrli, Birsfelden, both of Switzerland; Jean-Jacques Vorsanger, Hannut, Belgium

[73] Assignee: Hoffmann-La Roche Inc., Nutley, N.J.

[21] Appl. No.: 441,312

[22] Filed: Nov. 12, 1982

[30] Foreign Application Priority Data

Dec. 7, 1981 [CH] Switzerland ............... 7803/81
Aug. 18, 1982 [CH] Switzerland ............... 4940/82

[51] Int. Cl.³ ............... C07D 233/40; C07D 491/048; C07J 00/00
[52] U.S. Cl. ................... 548/303; 548/321; 260/239.5
[58] Field of Search ............ 260/239.5; 548/303, 548/321

[56] References Cited

U.S. PATENT DOCUMENTS 3,700,659 10/1972 Gerecke et al. ............ 260/239.5

*Primary Examiner*—Henry R. Jiles
*Assistant Examiner*—Kurt G. Briscoe
*Attorney, Agent, or Firm*—Jon S. Saxe; Bernard S. Leon; George W. Johnston

[57] ABSTRACT

A process for the manufacture of the optically active lactone of the formula

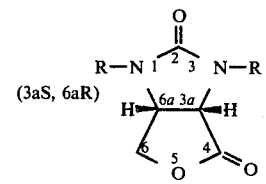

wherein R represents the benzyl group, is described.

In this process an optically active compound of the formula

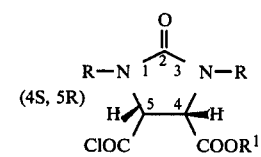

wherein R has the above significance and $R^1$ signifies the cholesteryl or the cyclohexyl group, is reduced with a dialkylaluminium hydride or a complex borohydride.

The compound of formula I is a known, valuable intermediate for, inter alia, (+)-biotin.

23 Claims, No Drawings

PROCESS AND INTERMEDIATES FOR THE MANUFACTURE OF (3aS, 6aR)-1,3-DIBENZYLDIHYDRO-1H-FURO[3,4-d]IMIDAZOLE-2,4(3H,3aH)-DIONE

BACKGROUND OF THE INVENTION

The present invention is concerned with a novel process for the manufacture of an optically active lactone of the formula

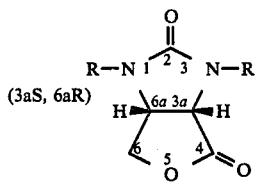

wherein R is benzyl.

This optically active lactone of formula I is a known, valuable intermediate in the synthesis of (+)-biotin, derivatives thereof and compounds related thereto.

Under the designation "(3aS,6aR)" used in connection with formula I there is to be understood in the scope of the present invention that antipode which is dextrorotatory in benzene or chloroform. This antipode is denoted hereinafter as the (+)-lactone.

A process for the manufacture of the (+)-lactone of formula I is already known from German patent specification No. 2 058 248 (corresponding to U.S. Pat. No. 3,700,659). In this process, racemic hemiesters of the formula

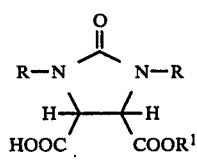

wherein R is benzyl and R¹ is cholesteryl or cyclohexyl, are separated into their optical antipodes and a desired antipode (i.e. the (+)antipode) is converted into the (+)-lactone of formula I. However, this process has the disadvantage that an undesired antipode, which results from the racemate resolution, must be recyclized before it can be converted to compound I.

There accordingly exists a need for a process wherein this undesired antipode can be converted into the desired (+)-lactone of formula I without recyclization. This need has been satisfied by the present invention. It has surprisingly been found that this undesired antipode, after conversion into the corresponding acid chloride, can be reduced selectively with a dialkylaluminum hydride or a complex borohydride to give the (+)-lactone of formula I.

SUMMARY

A process is disclosed for producing a (+)-lactone of the formula

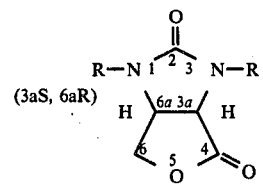

wherein R is benzyl,
by reducing an optically active compound of the formula

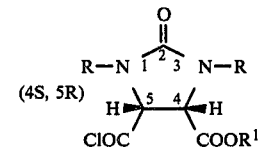

wherein R is as above and R¹ is cholesteryl or cyclohexyl, with a dialkylaluminum hydride or a complex borohydride to yield the (+)-lactone of formula I.

DETAILED DESCRIPTION OF THE INVENTION

The process in accordance with the invention comprises reducing an optically active compound of the formula

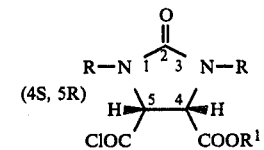

wherein R is benzyl and R¹ is cholesteryl or cyclohexyl, with a dialkylaluminium hydride or a complex borohydride to yield a (+)-lactone of the formula

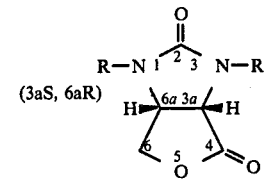

wherein R is as above.

Unless otherwise stated, "alkyl" denotes a straight-chain alkyl group of 1 to 12 carbon atoms or a branched-chain alkyl group of 3 to 12 carbon atoms. Exemplary straight-chain alkyl groups are methyl, ethyl, propyl, butyl, pentyl, hexyl, heptyl, octyl, nonyl, decyl, undecyl and dodecyl. Exemplary branched-chain alkyl groups are isopropyl, isobutyl, sec-butyl, 1-methylbutyl, 2-methylbutyl, 3-methylpentyl, 4-methylhexyl and isopentyl. Lower alkyl denotes straight-chain and branched-chain alkyl groups of 1 to 5 carbon atoms.

The term "halogen" ("halo") denotes fluorine, chlorine, bromine or iodine.

The term "alkali metal" denotes sodium, potassium or lithium.

In this application, a solid tapering line ( ▬▬ ) indicates that a substituent lies above the plane of the paper and a dashed line ( ---- ) indicates a substituent lies below the plane of the paper.

Under "dialkylaluminium hydrides" there are to be understood in the scope of the present invention aluminium hydrides whose alkyl groups contain preferably 2–8 carbon atoms and can be straight-chain or branched-chain. Examples of such aluminium hydrides are diethylaluminium hydride, diisobutylaluminium hydride (DIBAH), di-n-hexylaluminium hydride and the like.

Under "complex borohydrides" there are to be understood in the scope of the present invention especially those in which the cation can be an alkali metal such as lithium, sodium or potassium or a tetraalkylammonium ion such as tetrabutylammonium. Further, such complex borohydrides include those hydrides in which a hydrogen atom is replaced by a cyano group such as, for example, lithium, sodium or potassium cyanoborohydride.

In the resolution of the racemic compounds of formula A, the undesired antipodes are converted to a salt form by the bases used as the resolving agents, from which the corresponding optically active acids can then be liberated readily in a known manner. Any conventional resolution technique can be employed to produce such corresponding acids.

These resulting acids then can be converted into the optically active acid chlorides of formula II in a known manner. Any conventional process for converting such acids to their corresponding acid chlorides can be utilized. This conversion conveniently is carried out by means of a suitable halogenating agent in an inert organic solvent. Especially suitable halogenating agents are thionyl chloride, phosphorus trichloride, phosphorus pentachloride and the like. Thionyl chloride particularly is preferred. Typical inert organic solvents are aromatic and aliphatic hydrocarbons such as, for example, benzene, toluene, hexane, isooctane and the like.

In the above conversion of the acids to compound II, preferred inert organic solvents are aromatic hydrocarbons and especially benzene and toluene. The temperature and the pressure are not critical in this conversion which accordingly can be carried out at normal pressure (1 atm) and at temperatures of about room (23° C.) temperature to about 60° C.

The optically active acid chlorides of formula II are novel compounds and are also an object of the present invention.

In accordance with the invention the reduction of the compounds of formula II is carried out with a dialkylaluminium hydride or a complex borohydride. Lithium borohydride and sodium borohydride are preferred. Although not necessary the reaction conveniently is carried out in a solvent which is substantially inert towards acid chlorides and in which the hydrides are at least partially soluble. Convenient solvents are those usually used in connection with the corresponding hydrides such as, for example, aliphatic polyethers (e.g. monoglyme and diglyme) as well as tetrahydrofuran, dimethylformamide, toluene or mixtures or aqueous mixtures thereof.

In order that the desired reduction does not proceed too slowly and thus possibly give rise to undesired by-products, the aforementioned hydrides preferably are added in dissolved form to the reaction mixture.

Certain of the above hydrides can be used in an aqueous medium. Other hydrides are water-sensitive and preferably should not be used in an aqueous medium.

For reduction in aqueous medium, suitable solvents for the hydrides (which hydrides are usable in such medium) (e.g. sodium borohydride) are dimethylformamide, diglyme and especially water. The temperature range during such reduction is conveniently from about 40° C. to about −30° C., preferably from about 0° C. to about −30° C. and especially from about −10° C. to about −20° C.

Suitable solvents for reductions with water-sensitive hydrides (e.g. lithium borohydride or diisobutylaluminium hydride) are especially hydrocarbons such as toluene and the like or ethers such as tetrahydrofuran. The temperature range during such reduction is conveniently from about room temperature (23° C.) to about −20° C., preferably from about 10° C. to about −10° C. and especially from about 5° C. to about −5° C.

In the desired reduction, the pressure is not critical and the reaction can suitably be carried out at normal pressure. The amount of hydride used in the reduction in accordance with the invention is conveniently between about 0.5 and about 2.5 mol per mol of the acid chloride of formula II. When sodium borohydride is used, the preferred amount is about 1 to about 1.25 mol, when lithium borohydride is used the preferred amount is about 0.8 to about 0.85 mol and when DIBAH is used the preferred amount is about 2 mol, these amounts being calculated per mol of the acid chloride of formula II.

Since hydrolysis of the acid chloride function may also occur as a competing reaction to the reduction when aqueous systems are used, it is preferred to add the hydrides which are usable in aqueous medium rapidly and at a low temperature to the solution of the compound of formula II.

An especially preferred embodiment of the process in accordance with the invention comprises, reducing a solution of a compound of formula II in tetrahydrofuran, cooled to about −20° C., with an aqueous sodium borohydride solution.

A further preferred embodiment comprises reducing a solution of a compound of formula II in tetrahydrofuran or in toluene, cooled to about 0° C., with a solution of lithium borohydride in tetrahydrofuran.

The following non-limiting Examples illustrate the invention. Unless otherwise stated, percentages and ratios relating to solvent mixtures are expressed in volume, purity data determined by gas chromatography are expressed in area % and the remaining percentages and ratios are expressed in weight. Room temperature is about 23° C. Unless indicated otherwise, the Examples were carried out as written.

EXAMPLE 1

4.55 g (10 mmol) of cyclohexyl (4S,5R)-1,3-dibenzyl-5-chlorocarbonyl-2-oxo-4-imidazolidinecarboxylate are dissolved in 10 ml of tetrahydrofuran and the solution is cooled to −20° C. with a dry-ice/acetone bath. While stirring intensively there is then added dropwise a solution of 0.47 g (12.5 mmol) of sodium borohydride in 3 ml of water at such a rate that the temperature is held at −20° C. (dropwise addition time about 3 minutes). Thereupon, the cooling bath is removed and the mixture is stirred for a further 10 minutes. The temperature thereby rises from −20° C. to about 0° C. To the mixture are added dropwise within 5 minutes at 0° C. to −10° C. (ice-bath cooling) a solution of 8 ml of 25% hydrochloric acid and 30 ml of water. Strong foaming occurs at the beginning. The mixture is then stirred at 60° C. for 20 minutes and subsequently concentrated to about 15 ml in a water-jet vacuum. Thereto there are then added 15 ml of water and the mixture is left to stand at 0° C. for 1 hour. The crystallized-out crude product is filtered off under suction, rinsed with water and dried at 60° C. in vacuo for 4 hours. The crystallizate is dissolved in 15 ml of hot isopropanol and left to crystallize at 0° C. for 18 hours. The product is then filtered off under suction and rinsed twice with 5 ml of ice-cold isopropanol. After drying at 60° C. in vacuo for 6 hours, there is obtained a first crystallizate: 2.84 g (88%) with a melting point of 116°–117° C.

From the mother liquor there is obtained by crystallization from 3 ml of isopropanol and two-fold rinsing with 1 ml of isopropanol a second crystallizate: 0.30 g (9.3%) with a melting point of 116°–117° C.

The total yield accordingly amounts to 3.14 g (97%) of (3aS,6aR)-1,3-dibenzyldihydro-1H-furo[3,4-d]imidazole-2,4(3H,3aH)-dione. Melting point=116°–117° C.; $[\alpha]_D^{20} = +60.6°$ (1% in CHCl$_3$).

The cyclohexyl (4S,5R)-1,3-dibenzyl-5-chlorocarbonyl-2-oxo-4-imidazolidinecarboxylate used as the starting material can be prepared as follows:

4.365 g (10 mmol) of 4-cyclohexyl-5-hydrogen (4S,5R)-1,3-dibenzyl-2-oxo-4,5-imidazolidinedicarboxylate, 10 ml of toluene and 1.5 ml (20 mmol) of thionyl chloride are placed in a 100 ml sulphonation flask under an argon atmosphere and the mixture is stirred at 40° C. for 2 hours (the gas evolution has ended after about 1 hour). The toluene and the excess thionyl chloride are distilled off in a water-jet vacuum with a connected CO$_2$-cooling trap (oil-bath 55° C.). When the distillation has finished, it is cooled to room temperature and the vacuum is removed with argon. There are thus obtained 4.55 g of cyclohexyl (4S,5R)-1,3-dibenzyl-5-chlorocarbonyl-2-oxo-4-imidazolidinecarboxylate.

EXAMPLE 2

45.5 g (100 mmol) of cyclohexyl (4S,5R)-1,3-dibenzyl-5-chlorocarbonyl-2-oxo-4-imidazolidinecarboxylate (prepared according to Example 1) are dissolved in 50 ml of tetrahydrofuran. To the clear solution are added dropwise at 0° C. within 60 minutes 80 ml of a 1M lithium borohydride solution in tetrahydrofuran (80 mmol). The mixture is then stirred at 0° C. for a further 30 minutes. 100 ml of 1N hydrochloric acid are then cautiously added dropwise at 0° C. The mixture is then stirred at 70° C. for 30 minutes and subsequently concentrated in a rotary evaporator to 100 ml. Thereto there are added 200 ml of water and the mixture is left to crystallize at 0° C. for 18 hours. The crystallized-out crude product is filtered off under suction and washed neutral with water. After drying at 60° C. in vacuo for 4 hours, the crude product is dissolved in 100 ml of hot isopropanol and then left to crystallize at 0° C. for 18 hours. The product is then filtered off under suction and rinsed twice with 20 ml of ice-cold isopropanol each time. After drying at 60° C. in a water-jet vacuum for 6 hours, there are obtained 26.5 g of (3aS,6aR)-1,3-dibenzyldihydro-1H-furo[3,4-d]imidazole-2,4(3H,3aH)-dione with a melting point of 116°–117° C.

From the mother liquor there are obtained by crystallization a further 2.35 g of product with a melting point of 116°–117° C. The total yield is 28.85 g (89.5% of theory).

We claim:

1. A process for manufacturing an optically active lactone of the formula

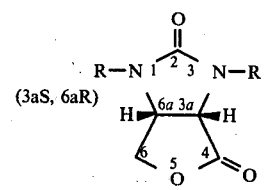

wherein R is benzyl, comprising reducing an optically active compound of the formula

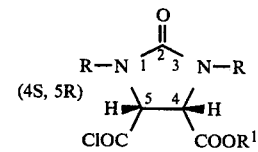

wherein R is as above and R$^1$ is cholesteryl or cyclohexyl, with a dialkylaluminium hydride or a complex borohydride to produce lactone I.

2. The process of claim 1 wherein the complex borohydride is sodium borohydride.

3. The process of claim 1 wherein the reduction comprises:
   (a) dissolving compound II in tetrahydrofuran to form a first solution; and
   (b) reducing the first solution with an aqueous sodium borohydride solution to produce lactone I.

4. The process of claim 1 wherein the reduction is carried out at a temperature from about 40° C. to about −30° C.

5. The process of claim 4 wherein the reduction is carried out at a temperature from about 0° C. to about −30° C.

6. The process of claim 5 wherein the reduction is carried out at a temperature from about −10° C. to about −20° C.

7. The process of claim 2 wherein the reduction is carried out at a temperature from about 40° C. to about −30° C.

8. The process of claim 7 wherein the reduction is carried out at a temperature from about 0° C. to about −30° C.

9. The process of claim 8 wherein the reduction is carried out at a temperature from about −10° C. to about −20° C.

10. The process of claim 1 wherein the complex borohydride is lithium borohydride.

11. The process of claim 1 wherein the reduction comprises:
   (a) dissolving compound II in tetrahydrofuran or toluene to form a first solution; and
   (b) reducing the first solution with a second solution of lithium borohydride in tetrahydrofuran to produce lactone I.

12. The process of claim 1 wherein the reduction is carried out at a temperature from about 23° C. to about −20° C.

13. The process of claim 12 wherein the reduction is carried out at a temperature from about 10° C. to about −10° C.

14. The process of claim 13 wherein the reduction is carried out at a temperature from about 5° C. to about −5° C.

15. The process of claim 10 wherein the reduction is carried out at a temperature from about 23° C. to about −20° C.

16. The process of claim 15 wherein the reduction is carried out at a temperature from about 10° C. to about −10° C.

17. The process of claim 16 wherein the reduction is carried out at a temperature from about 5° C. to about −5° C.

18. The process of claim 1 wherein the dialkylaluminium hydride or complex borohydride is present in an amount of about 0.5 to about 2.5 mol per mol of compound II.

19. A process for manufacturing an optically active lactone of the formula

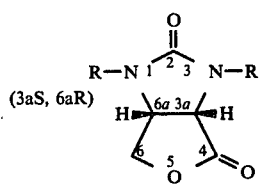
I wherein R is benzyl, comprising
(a) dissolving an optically active compound of the formula

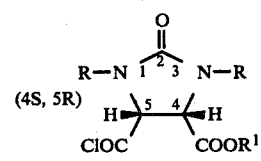
II wherein R is as above and R¹ is cholesteryl or cyclohexyl in tetrahydrofuran to form a first solution; and
(b) then, at a temperature between about −10° C. and about −20° C. reducing the first solution with an aqueous sodium borohydride solution to yield lactone I.

20. A process for manufacturing an optically active lactone of the formula

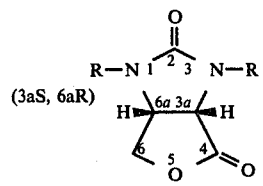
I wherein R is benzyl, comprising
(a) dissolving an optically active compound of the formula

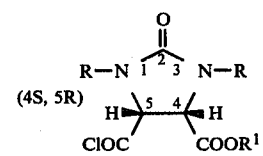
II wherein R is as above and R¹ is cholesteryl or cyclohexyl in tetrahydrofuran to form a first solution; and
(b) then, at a temperature between about 5° C. and about −5° C., reducing the first solution with a second solution of lithium borohydride in tetrahydrofuran to yield lactone I.

21. An optically active compound of the formula

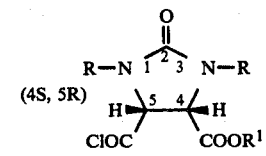
II wherein R¹ is cholesteryl or cyclohexyl and R is benzyl.

22. The compound of claim 21 wherein R¹ is cholesteryl.

23. The compound of claim 21 wherein R¹ is cyclohexyl.

* * * * *